United States Patent
Kurz et al.

(10) Patent No.: US 6,852,677 B2
(45) Date of Patent: Feb. 8, 2005

(54) POLYOXYMETHYLENE MOULDING COMPOUND CONTAINING A LUBRICANT, THE USE THEREOF AND MOULDED BODIES PRODUCED THEREFROM

(75) Inventors: Klaus Kurz, Kelsterbach (DE); Oskar Schleith, Hofheim (DE)

(73) Assignee: Ticona GmbH (DE)

( * ) Notice: Subject to any disclaimer, the term of this patent is extended or adjusted under 35 U.S.C. 154(b) by 125 days.

(21) Appl. No.: 10/311,162

(22) PCT Filed: May 31, 2001

(86) PCT No.: PCT/EP01/06231

§ 371 (c)(1),
(2), (4) Date: Mar. 26, 2003

(87) PCT Pub. No.: WO01/96470

PCT Pub. Date: Dec. 20, 2001

(65) Prior Publication Data

US 2003/0171470 A1 Sep. 11, 2003

(30) Foreign Application Priority Data

Jun. 15, 2000 (DE) .......................... 100 29 533

(51) Int. Cl.$^7$ ...................... C10M 163/00; C08K 5/103; C08K 5/101
(52) U.S. Cl. ........................ 508/100; 508/109; 524/275
(58) Field of Search ................................. 508/100, 109; 524/275, 300, 306–318

(56) References Cited

U.S. PATENT DOCUMENTS

| | | | | |
|---|---|---|---|---|
| 4,493,751 A | * | 1/1985 | Cherdron et al. | 162/157.2 |
| 5,416,152 A | | 5/1995 | Fleischer et al. | 524/487 |
| 5,559,180 A | | 9/1996 | Takahashi et al. | 524/512 |
| 5,641,824 A | * | 6/1997 | Forschirm | 524/317 |
| 5,679,743 A | * | 10/1997 | Hirai et al. | 525/88 |
| 6,046,141 A | | 4/2000 | Kurz et al. | 508/100 |
| 6,211,268 B1 | * | 4/2001 | Matsumura et al. | 524/100 |
| 6,391,956 B1 | * | 5/2002 | Horio et al. | 524/314 |

FOREIGN PATENT DOCUMENTS

| | | |
|---|---|---|
| DE | 2947490 | 11/1979 |
| EP | 548692 | 3/1997 |
| EP | 589354 | 4/1997 |
| WO | 99/35191 | 7/1999 |

* cited by examiner

*Primary Examiner*—Matthew A. Thexton
(74) *Attorney, Agent, or Firm*—Connolly Bove Lodge & Hutz LLP

(57) ABSTRACT

Polyoxymethylene with addition of a lubricant mixture composed of an aliphatic ester and of a polyethylene wax improves in-feed behavior into the injection-molding machine without substantially changing tribological behavior, when comparison is made with a polyoxymethylene which has only an aliphatic ester. The weld-line strength of the molding is also improved. The molding composition is used for moldings of any type with high tribological requirements running against hard materials.

15 Claims, No Drawings

POLYOXYMETHYLENE MOULDING COMPOUND CONTAINING A LUBRICANT, THE USE THEREOF AND MOULDED BODIES PRODUCED THEREFROM

The invention relates to a lubricant-modified polyoxymethylene comprising a mixture of an aliphatic ester and a polyethylene wax, and to its use.

Polyoxymethylene homo- and copolymers with an incorporated aliphatic ester have very low coefficients of friction and low abrasion in tribological pairing with plastics or metallic materials, particularly with steel. An example of the coefficient of friction of a polyoxymethylene (POM) provided with ester wax can be 40% lower than that of the respective unmodified material.

Polyoxymethylene molding compositions of this type are well known, for example the polyacetal molding compositions described in U.S. Pat. No. 5,559,180 and EP 589354, which may comprise, inter alia, fatty esters. Molding compositions which comprise relatively small amounts of polyethylene waxes are known from EP 548692, for example, but these materials were not developed for use in tribological applications.

However, the positive tribological properties of the abovementioned mixture of POM with aliphatic ester leads to problems during the processing of these products. Since producers of processing machinery, such as extruder and injection-molding machinery, use exclusively steel screws for preparing the melt, conveying problems arise with these screws in the in-feed zones, due to the low coefficient friction. This can lead to very long feed times and thus to uneconomic cycle times when producing moldings, due to the low level of friction between pellets and steel screw. In the most disadvantageous case, the material is not drawn into the screw at all.

Some assistance is usually obtained by applying small amounts of metal salts of a carboxylic acid in a drum mixer. However, industrial use of this procedure requires a very large amount of work.

Incorporation of these metal salts into the product is also possible. However, the concentrations which have to be used here are markedly higher than during application in a drum mixer. They can reduce the level of mechanical properties of the polymer. In addition, deposits in the mold and discoloration on the finished part are often found during injection molding.

It is therefore the object of the present invention to improve in-feed behavior of an aliphatic-ester-modified polyoxymethylene, reducing the pull-off in mechanical properties caused by the additives, and retaining good tribological properties.

This object is achieved by means of a thermoplastic molding composition comprising
    component (A) from 40 to 99.5 parts by weight of a polyoxymethylene homo- or copolymer,
    component (B) from 0.5 to 10 parts by weight of a lubricant mixture,
    component (C) from 0 to 60 parts by weight of additives,
    where the lubricant mixture comprises an aliphatic ester and a polyethylene wax, and the entirety of components (A), (B), and (C) is always 100 parts by weight.

Surprisingly, it has been found that the mixture of aliphatic esters and polyethylene waxes brings about a compromise between good lubricant action, little fall-off in mechanical properties, and acceptable in-feed performance into the processing machinery. The advantages of the mixture are:

in-feed performance into the processing machinery is improved
    there is less severe fall-off in mechanical properties within the weld line of the polyoxymethylene
    there is no change in wear of the finished parts within the limits of measurement accuracy of tribological measurements when the results are compared with POMs which comprise an aliphatic ester without any addition of polyethylene wax.

The object was therefore achieved by using a lubricant mixture which also includes, besides the ester, polyethylene wax, preference being given to a high-molecular-weight oxidized (polar) polyethylene wax. Although polyethylene waxes are likewise lubricants with surface action, i.e. also have good frictional properties with respect to steel, they do not have the high level of release action of the aliphatic esters, e.g. the ester waxes.

The polyoxymethylene homo- or copolymer mentioned in the introduction is suitable as component (A). Polyoxymethylenes (POMs), for example as described in DE-A 29 47 490, are generally unbranched linear polymers which generally contain at least 80%, preferably at least 90%, of oxymethylene units ($—CH_2O—$). The term polyoxymethylenes here encompasses homopolymers of formaldehyde or of its cyclic oligomers, such as trioxane or tetroxane, and also appropriate copolymers.

Homopolymers of formaldehyde or of trioxane are polymers whose hydroxy end groups have been stabilized chemically in a known manner with respect to degradation, e.g. by esterification or etherification. Copolymers are polymers of formaldehyde or of its cyclic oligomers, in particular trioxane, with cyclic ethers, with cyclic acetals, and/or with linear polyacetals.

POM homo- or copolymers are known per se to the skilled worker and have been described in the literature. Very generally, these polymers have at least 50 mol % of $—CH_2O—$ repeat units in the main polymer chain. The homopolymers are generally prepared by polymerizing formaldehyde or trioxane, preferably in the presence of suitable catalysts.

For the purposes of the invention, POM copolymers are preferred as component (A), in particular those which besides the $—CH_2O—$ repeat units also contain up to 50 mol %, preferably from 0.1 to 20 mol %, and in particular from 0.5 to 10 mol %, of repeat units

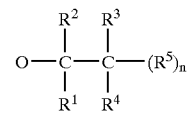

where $R^1$ to $R^4$, independently of one another, are a hydrogen atom, a $C_1$–$C_4$-alkyl group, or a halogen-substituted alkyl group having from 1 to 4 carbon atoms, and $R^5$ is $—CH_2—$, $—CH_2O—$, a $C_1$–$C_4$-alkyl-substituted or $C_1$–$C_4$-haloalkyl-substituted methylene group, or a corresponding oxymethylene group, and n is a value in the range from 0 to 3. These groups may advantageously be introduced into the copolymers via ring-opening of cyclic ethers. Preferred cyclic ethers are those of the formula

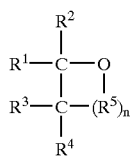

where $R^1$ to $R^5$ and n are as defined above. Merely by way of example, mention may be made of ethylene oxide, propylene 1,2-oxide, butylene 1,2-oxide, butylene 1,3-oxide, 1,3-dioxane, 1,3-dioxalane, and 1,3-dioxepan as cyclic ethers, and also linear oligo- or polyformals, such as polydioxolane or polydioxepan as comonomers. Copolymers of from 99.5 to 95 mol % of trioxane and from 0.5 to 5 mol % of one the abovementioned comonomers are particularly advantageous.

Oxymethylene terpolymers are also a suitable component (A) and are obtained, for example, by reacting trioxane with one of the above-described cyclic ethers and with a third monomer, preferably a bifunctional compound of the formula

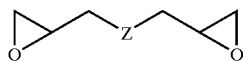

where Z is a chemical bond, —O—, or —ORO— (R=$C_1$–$C_8$-alkylene or $C_2$–$C_8$-cycloalkylene).

Preferred monomers of this type are ethylene diglycide, diglycidyl ether, and diethers composed of glycidyl units and formaldehyde, dioxane, or trioxane in a molar ratio of 2:1, and also diethers composed of 2 mol of glycidyl compound and 1 mol of an aliphatic diol having from 2 to 8 carbon atoms, for example the diglycidyl ethers of ethylene glycol, 1,4-butanediol, 1,3-butanediol, 1,3-cyclobutanediol, 1,2-propanediol, or 1,4-cyclohexanediol, to mention just a few examples.

Processes for preparing the polyoxymethylene homo- and copolymers described above are known to the skilled worker and are described in the literature.

The preferred POM copolymers having melting points of at least 150° C. and molecular weights (weight-average) $M_w$ in the range from 5000 to 200,000, preferably from 7000 to 150,000. Particular preference is given to end-group-stabilized POMs whose chain ends have carbon-carbon bonds. The POMs used generally have a melt index (MVR 190/2, 16) of from 2 to 50 cm$^3$/10 min (ISO 1133).

As lubricant mixture (B), the molding composition of the invention comprises a mixture of at least one aliphatic ester and at least one polyethylene wax. The molding composition of the invention preferably comprises from 1 to 3 parts by weight of the lubricant mixture (B). The lubricant mixture (B) is preferably composed of an aliphatic ester and of a polyethylene wax in a ratio of 1:2 parts by weight. Examples of aliphatic esters are: esters of saturated or unsaturated aliphatic carboxylic acids, preferably those which contain from 10 to 100 carbon atoms, particular preference being given to ester waxes, stearyl stearate, behenyl behenate, isostearyl stearate, glycerol monostearate, glycerol monoisostearate, glycerol distearate, pentaerythritol tetrastearate, pentaerythritol tetrabehenate, montanic esters, and partially hydrolyzed montanic esters. It is also possible to use mixtures of various esters in any desired mixing ratios.

Polyethylene waxes which may be used are waxes with a density of from 0.92 to 0.98 g/cm$^3$ and with a drop point of from 100 to 145° C., and with a viscosity number at 140° C. of from 100 to 100,000 mPa s. Here again, mixtures in any desired ratio may be used.

The polyethylene waxes used preferably comprise oxidized polyethylene waxes. The preferred oxidized polyethylene wax is a high-molecular-weight polar wax and generally has an acid value of from 5 to 60 mg KOH/g, advantageously from 5 to 50 mg KOH/g, in particular from 5 to 25 mg KOH/g, and a viscosity of from 3000 to 100,000 mPa*s at 140° C.

The particular feature of the oxidized polyethylene wax is the functional groups oxygen-bonded to the surface. They are produced in a controlled manner by oxidative post treatment. The oxidative post treatment of the polyethylene wax improves affinity to the POM. When comparison is made with other polyethylene waxes, the pull-off in weld line extensibility is less marked, and the abrasion during sliding is smaller. This additional advantage is also known from EP 0 905 190. Lubricants suitable for use in the lubricant mixture of the invention are also described in G ächter/Müller, "Taschenbuch der Kunststoff-Additive [Plastics additives handbook]", 3rd Edition, Carl Hanser Vedag Munich, Vienna, 1994, pp. 478–504, incorporated herein by way of reference.

Additives (C) may be processing aids, fillers, reinforcing materials, and/or polymeric lubricants. Examples which may be mentioned, but without limiting the scope to the examples mentioned, are formaldehyde scavengers, acid scavengers, antioxidants, UV stabilizers, coupling agents, nucleating agents, and mold-release agents, or else carbon fibers, aramid fibers, glass fibers, glass beads, calcium carbonate, wollastonite, silicon dioxide, and additional lubricants, and also mixtures of these. Examples of additional lubricants are ultra-molecular-weight polyethylene (UHMWPE), polytetrafluoroethylene (PTFE), and graft copolymer, which is a product of a graft reaction of an olefin polymer and an acrylonitrile-styrene copolymer, and other examples are mixtures of these.

The entirety of components (A) to (C) always gives 100 parts by weight here. The lubricant-modified polyoxymethylene of the invention has improved processability, and weld line strength is increased when comparison is made with a POM modified only with aliphatic esters at comparable concentrations. The good frictional and wear performance is substantially retained. The material is suitable for producing moldings of any type. The tribological properties of the material are of particular benefit in the form of a sliding partner for metallic materials, particularly for steel, or else for relatively hard plastics, such as polybutylene terephthalate. The examples below are intended to provide the skilled worker with an illustration of the advantages of the present invention.

EXAMPLES

For Comparative Example A and Inventive Examples 1 to 4 use is made of a copolymer of trioxane and dioxolane with a volume melt index MVR 190/2, 16 of 8 cm$^3$/10 min. The copolymer was treated with the additives listed in Table 1.

TABLE 1

| Constituents of mixing specification in parts by wt. | Example A comparison | Example 1 | Example 2 | Example 3 | Example 4 |
|---|---|---|---|---|---|
| POM copolymer | 98 | 98 | 98 | 98 | 98 |
| Ester wax | 2 | 1.2 | 1.0 | 0.8 | 0.6 |
| Oxidized PE wax | — | 0.8 | 1.0 | 1.2 | 1.4 |

The POM copolymer was mixed in a high-speed Diosna V 100 fluid mixer (Dierks u. Söhne, Osnabrück, Germany) with the respective additives, and melted in a twin-screw ZE 25×33 D extruder (Berstorff, Hanover, Germany), the temperature of the composition being 200° C., and then pelletized. The pellets were dried for eight hours at 120° C. and then injection-molded to give test specimens for mechanical and tribological tests. The injection-molding machine used was a KM 90/210 B (Krauss Maffei, Munich, Germany). The processing conditions were selected in accordance with the recommendations of ISO 9988-2, materials standard for POM.

Measurements:
Rheological Properties
    MVR 190/2, 16 to ISO 1133
Mechanical Properties
    Tensile test to ISO 527, Parts 1 and 2
Wear Measurements Abrasion was measured on an abrasion shaft, a rotating shaft onto which cylindrical test specimens of diameter 12 mm made from the material to be tested were pressed. Wear volume is determined as a function of time. The principle of the test corresponds to the "pin on ring" principle of ISO/DIS 7148-2.

Test Conditions:

| Material of shaft | Steel |
|---|---|
| Shaft diameter | 65 mm |
| Roughness depth Rz | about 0.8 μm |
| Load | 3.1 N |
| Sliding velocity | 136 m/min |
| Duration of experiment | 60 h |

Determination of Coefficient of Friction

The coefficient of friction was determined on a test rig with an oscillating movement. A ball is pressed, using a defined normal force, onto the sheet produced from the material to be tested and moving backward and forward. Due to friction, the sheet attempts to move the ball, which has been suspended on sheet springs. The frictional force measured by inductive sensors is divided by the normal force to give the coefficient of friction.

Test Conditions:

Test specimen a) steel ball 12.7 mm Ø

Test specimen b) sheet 20×10×4 mm

The test results are listed in Table 2.

TABLE 2

| Feature | Example A comparison | Example 1 | Example 2 | Example 3 | Example 4 |
|---|---|---|---|---|---|
| MVR 190/2, 16 [cm$^3$/10 min] | 8.6 | 8.5 | 8.6 | 8.7 | 8.7 |
| Injection-molding machine feed time [s] | *) | 32 | 31.2 | 28.8 | 27.9 |
| Weld line strength [MPa] | 47.5 | 59 | 59 | 60 | 61 |
| Tensile strain at break at weld line [%] | 3.8 | 7.0 | 7.0 | 7.8 | 9.2 |
| Wear volume [mm$^3$] | 0.62 | 0.68 | 0.71 | 0.71 | 0.77 |
| Coefficient of friction | 0.19 | 0.24 | 0.24 | 0.27 | 0.3 |

*) The material could not be processed without pretreatment (application of 0.1% of magnesium stearate in a drum mixer).

The examples show that in-feed performance into the injection-molding machine is improved for the mixtures of ester wax with oxidized polyethylene wax (mixing specifications 1–4) when comparison is made with ester wax alone (mixing specification A), i.e. feed time is reduced with increasing content of oxidized polyethylene wax. An increase in weld line strength is also observed. The wear volume in the tribological tests remains substantially identical within the bounds of accuracy of measurement. However, Examples 1–4 also show that the coefficient of friction increases as the amount of polyethylene wax increases. Care therefore needs to be taken in balancing the wax ester/polyethylene wax lubricant mixture for applications needing minimized coefficient of friction.

What is claimed is:

1. A thermoplastic molding composition comprising
    component (A) from 40 to 99.5 parts by weight of a polyoxymethylene homo- or copolymer,
    component (B) from 0.5 to 10 parts by weight of a lubricant mixture,
    component (C) from 0 to 60 parts by weight of additives, where the lubricant mixture comprises an ester of an aliphatic carboxylic acid having from 10 to 100 carbon atoms and a polyethylene wax, and the entirety of components (A), (B), and (C) is always 100 parts by weight.

2. The molding composition as claimed in claim 1, wherein the lubricant mixture, component (B), comprises said ester and said polyethylene wax in a ratio of 1:100 to 100:1 parts by weight.

3. The molding composition as claimed in claim 1, wherein the lubricant mixture, component (B), comprises said ester and said polyethylene wax in a ratio of 1:2 parts by weight.

4. The molding composition as claimed in claim 2, wherein the lubricant mixture, component (B), comprises said ester and said polyethylene wax in a ratio of 1:2 parts by weight.

5. The molding composition as claimed in claim 1, wherein the molding composition comprises from 1 to 3 parts by weight of the lubricant mixture, component (B).

6. The molding composition as claimed in claim 4, wherein the molding composition comprises from 1 to 3 parts by weight of the lubricant mixture, component (B).

7. The molding composition as claimed in claim 1, wherein said polyethylene wax is a high-molecular-weight polyethylene wax with an acid value of from 5 to 60 mg KOH/g and with a viscosity of from 3000 to 100,000 mPa*s at a temperature of 140° C.

8. The molding composition as claimed in claim 6, wherein said polyethylene wax is a high-molecular-weight polyethylene wax with an acid value of from 5 to 60 mg KOH/g and with a viscosity of from 3000 to 100,000 mPa*s at a temperature of 140° C.

9. The molding composition as claimed in claim 1, wherein said polyethylene wax is an oxidized polyethylene wax.

10. The molding composition as claimed in claim 8, wherein said polyethylene wax is an oxidized polyethylene wax.

11. The molding composition as claimed in claim 1, wherein component (C) is one or more components selected from the group consisting of filler chalk, talc, wollastonite, mica, zinc oxide, silicon dioxide, glass fiber, aramid fiber, carbon fiber, organic high-modulus fiber, polymeric lubricant, polytetrafluoroethylene in powder form, polytetrafluoroethylene in fiber form, ultra high molecular weight (UHMW) polyethylene and graft polymer obtained from the graft reaction of polyethylene, acrylonitrile-styrene copolymer (SAN).

12. The molding composition as claimed in one claim 10, wherein component (C) is one or more components selected from the group consisting of filler chalk, talc, wollastonite, mica, zinc oxide, silicon dioxide, glass fiber, aramid fiber, carbon fiber, organic high-modulus fiber, polymeric lubricant, polytetrafluoroethylene in powder form, polytetrafluoroethylene in fiber form, ultra high molecular weight (UHMW) polyethylene and graft polymer obtained from the graft reaction of polyethylene, acrylonitrile-styrene copolymer (SAN).

13. A film which comprises the thermoplastic molding composition as claimed in claim 1.

14. A molding produced from the thermoplastic molding composition as claimed in claim 1.

15. The molding as claimed in claim 14, wherein the molding is used as a sliding partner for metallic materials or for relatively hard plastics.

* * * * *

UNITED STATES PATENT AND TRADEMARK OFFICE
CERTIFICATE OF CORRECTION

PATENT NO.    : 6,852,677 B2                                           Page 1 of 1
DATED         : February 8, 2005
INVENTOR(S)   : Klaus Kurz et al.

It is certified that error appears in the above-identified patent and that said Letters Patent is hereby corrected as shown below:

Column 8,
Line 9, "claimed in one claim 10," should read -- claimed in claim 10 --.

Signed and Sealed this

Twenty-eighth Day of June, 2005

JON W. DUDAS
*Director of the United States Patent and Trademark Office*